United States Patent [19]

Eckenhoff

[11] Patent Number: 4,753,651
[45] Date of Patent: * Jun. 28, 1988

[54] SELF-DRIVEN PUMP

[75] Inventor: James B. Eckenhoff, Los Altos, Calif.

[73] Assignee: ALZA Corporation, Palo Alto, Calif.

[*] Notice: The portion of the term of this patent subsequent to Jul. 20, 1999 has been disclaimed.

[21] Appl. No.: 412,465

[22] Filed: Aug. 30, 1982

[51] Int. Cl.[4] .................................................. A61K 9/00
[52] U.S. Cl. ......................................... 424/449; 604/51
[58] Field of Search .............. 604/896, 890, 891, 892, 604/51-53, 93, 31, 150, 151

[56] References Cited

U.S. PATENT DOCUMENTS 4,340,048 7/1982 Eckenhoff .......................... 604/896

Primary Examiner—C. Fred Rosenbaum
Assistant Examiner—H. Macey
Attorney, Agent, or Firm—Steven F. Stone; Paul L. Sabatine; Edward L. Mandell

[57] ABSTRACT

A self-driven pump that delivers a flowable composition at a constant baseline rate and may be manipulated to supplement the baseline rate with one or more pulses of the composition. One pump embodiment consists of a rigid hollow housing with one fixed end wall and one axially moveable end wall; an axially slideable water imbibing assembly mounted transversely in the housing lumen that divides the lumen into a first compartment containing the composition to be dispersed and a second liquid to be imbibed, preferably water, containing compartment. An outlet port extends through the wall of the housing into the first compartment. In operation the subassembly imbibes water from the second compartment and expands into the first compartment to displace the composition therefrom through the outlet at the baseline rate. Pulses are effected by depressing the axially moveable end wall which in turn slides the subassembly toward the fixed end wall thereby exerting pressure on the composition to be dispersed and increasing the injection rate.

20 Claims, 2 Drawing Sheets

SELF-DRIVEN PUMP

TECHNICAL FIELD

This invention relates to self-driven pumps capable of delivering controlled amounts of a fluid over a prolonged period of time and are particularly useful for administering pharmaceutical preparations to a patient according to a controlled dosage regimen.

RELATED PATENT APPLICATION

This patent application is related to my patent for Self Driven Hypodermic Injector, U.S. Pat. No. 4,340,048, July 20, 1982.

BACKGROUND ART

The hypodermic syringe is perhaps the most common hypodermic injector. It consists of a barrel fitted with a plunger and a hollow needle. Mechanically driven syringes are employed to infuse drugs into patients continuously over relatively long periods.

U.S. Pat. Nos. 3,814,097, 3,964,482, and 4,159,720 disclose devices for administering drugs percutaneously on a continuous basis that include integral components that penetrate the skin. The latter employes wicks or monofilaments that are installed in the subcutaneous flesh and are connected to a drug reservoir attached to the skin surface. The drug is transported from the reservoir into the flesh by capillary action. The other two patents use hollow skin piercing projections that extend from the undersides of the respective devices.

A variety of osmotically driven fluid dispensers or injectors are either available commercially or described in the literature. These dispensers operate by imbibing water through a semipermeable membrane to displace fluid, typically a drug or other active agent, from the dispenser. Rose and Nelson, Austral. J. Exp. Biol., 1955, 33, pp. 415–420 describes one such injector. Its main components are a glass ampoule, two latex bags, and a semipermeable cellophane membrane mounted in a ring clamp. The ampoule has a nipple at one of its ends and a splayed mouth at the other end. One of the latex bags is partly collapsed, contains a saturated solution of Congo Red, and is tied over the clamp at a point below the bag mouth. This bag is placed in the ampoule with its edge tied over the splay of the ampoule mouth. The second bag is filled with water and its mouth is also tied over the splay of the ampoule mouth. Drug is contained in the space within the ampoule not occupied by the ring-first bag assembly. In operation, water is imbibed osmotically from the second bag through the cellophane member into the first bag causing he first bag to inflate. This inflation displaces drug from the ampoule via the nipple.

U.S. Pat. No. 3,604,417 describes another such injector which consists of three rigid chambers arranged in tandem. The first chamber contains the drug and has an outlet. The second contains a solution of an osmotically effective solute and is separated from the first by a piston. The third contains water and is separated from the second by a semipermeable membrane. In operation, water from the third chamber is imbibed through the semipermeable membrane into the second chamber due to an osmotic imbalance between the contents of the two chambers. The influx of water into the second chamber drives the piston that separates the second and first chambers into the first chamber, thereby displacing drug therefrom via the outlet.

U.S. Pat. No. 3,987,790 describes another type of osmotically driven dispenser. Its basic components are an inner flexible bag that contains the fluid to be dispensed, an intermediate layer of an osmotically effective composition that encapsulates the inner bag, an outer rigid semipermeable coating that encapsulates both the inner bag and intermediate layer, and an outlet/filling port that communicates with the interior of the inner bag. In operation the inner bag is charged with the fluid to be dispensed via the filling/discharge port and the dispenser is placed in an aqueous environment, such as a body cavity or within body tissue. Water is imbibed from the environment by the osmotically effective composition through the semipermeable coating into the space between the coating and the inner bag. Since the bag is flexible and the coating is rigid, the imbibed water squeezes the bag inwardly thereby displacing fluid from the bag via the discharge/filling port.

A principal object of the present invention is to provide a self-driven pump that will deliver a fluid formulation at a constant controlled rate.

Another object of the present invention is to provide such pump whose component parts align axially and thus may be assembled easily.

Yet another object of the present invention is to provide such pump that includes means for supplementing the constant delivery rate with one or more pulse injections of the fluid formulation.

DISCLOSURE OF THE INVENTION

The invention is a self-driven pump that is particularly suitable for use to deliver a pharmaceutical composition into a patient according to a controlled dosage regimen. The components of the pump are: (1) a hollow closed body; (2) a liquid, preferably water, imbibing subassembly mounted within the body that divides the lumen of the body into two compartments one of which hold the fluid composition to be pumped and the other of which holds the source of the liquid to be imbibed and (3) an outlet conduit, that extends through the wall of the body to the fluid composition-containing compartment. The outlet conduit may be adapted to be connected to a hollow tube, catheter or needle, for example to conduct the fluid to its situs of use. The liquid-imbibing assembly includes a rigid semipermeable wall that faces the liquid-containing compartment, an expandable impermeable wall that faces the fluid composition-containing compartment, and a liquid-imbibing composition between the semipermeable and impermeable walls. When the pump is used to deliver a pharmaceutical composition the outlet may be connected to a needle which penetrates the skin at the location of the pump or to a catheter which is connected to a remote needle or a Y fitting in an IV line or a force feeding line for example.

MODES FOR CARRYING OUT THE INVENTION

Figure 1:
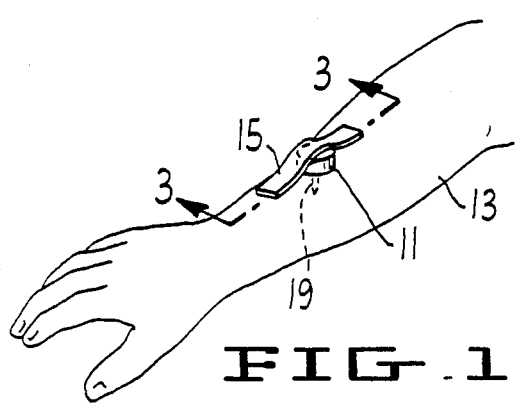
FIG. 1 is a perspective view of the prferred embodiment of the invention pump attached to the arm of a patient.
Figure 7:
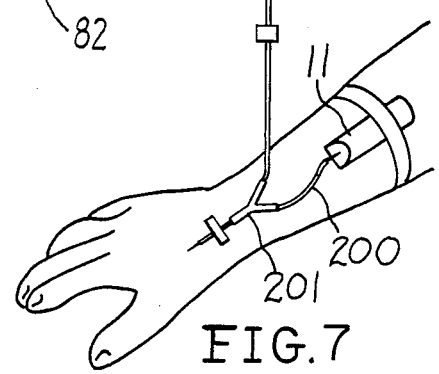
FIG. 7 shows an embodiment of this invention connected to a line for introducing fluid at a remote location.

FIGS. 1–3 and 7 illustrate a pump, generally designated 11, that is capable of delivering a fluid composition 12 (FIG. 3) at a substantially constant rate with or without one or more manually instigated pulses. Pump 11 may be cylindrical and when used to deliver pharmaceutical compositions may be adapted to be placed on the patient's skin, such as on forearm 13, with one of its ends 14 defining a basal surface that rests against the skin as shown in FIG. 1. If need be, an adhesive overlay 15 or other affixation means may be employed to keep the injector positioned firmly on the skin. Alternatively the pump 11 may be mounted on its side which may be flattened as shown in FIG. 7. Instead of entering the skin directly the outlet may be connected to a catheter 200 for delivery to a remote location such as a Y-fitting 201 connected to a standard IV set shown generally as 202.

Figure 2:
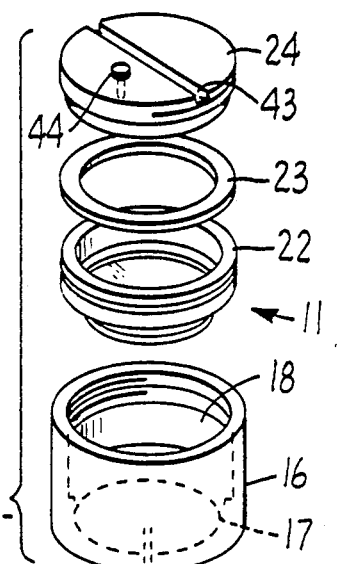
FIG. 2 is an exploded view of the pump of FIG. 1.
Figure 3:
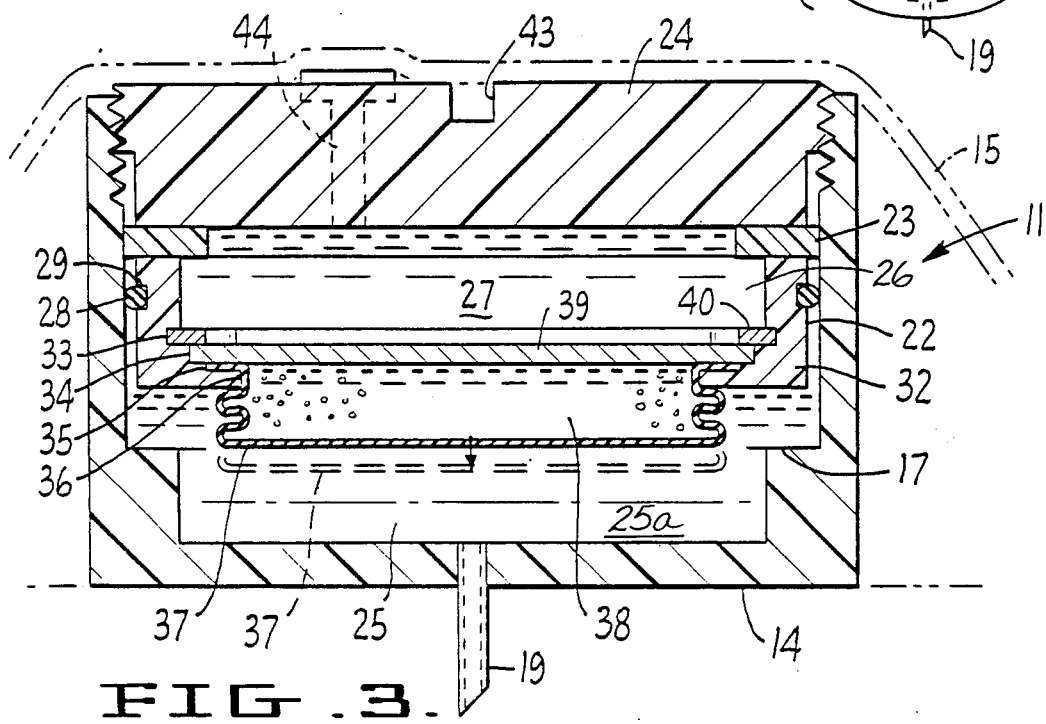
FIG. 3 is an enlarged sectional view of the pump of FIG. 1 taken along line 3—3 of FIG. 1.

The basic components of pump 11 and their axial relationship are shown in FIG. 2. Those components are: a hollow housing 16 that includes integral end 14, has an internal shoulder 17, and is threaded on its inner surface near its open end 18; an outlet 19 extending through end 14 to the cylindrical lumen of the housing and which projects outward from end 14; an axially slideable subassembly 22 that carries the water-imbibing means of the pump and is received within the cylindrical lumen of the housing; a low friction washer 23 that is also received within the housing lumen; and an externally threaded end cap 24 that screws into the open end of the housing to close same. FIG. 3 shows these components in their assembled position with the pump charged with the fluids that make it operational.

As seen in FIG. 3, subassembly 22 divides the cylindrical lumen of the housing into a first compartment 25 that is contiguous to end 14 and contains the composition 25a to be pumped and a second compartment 26 that is contiguous to the end cap and contains an osmotically active, preferably aqueous liquid 27. Liquid 27 may be present as the free liquid per se, or as a gel such as a hydrogel or may be absorbed on a fibrous or porous wick or mat, for example. Subassembly 22 is slideably mounted within the housing by means of an O-ring 28 that is seated in a channel 29 formed in the exterior surface of the subassembly. The O-ring forms the principal seal between compartments 25 and 26 to prevent contamination of the composition to be pumped by the osmotically active liquid. Subassembly 22 is composed of an outer support ring 32 whose inner circumferential surface has a channel 33 and a trio of stepped shoulders 34, 35, 36 into and on which the other components of the subassembly are mounted. An elastomeric bellows-like impermeable bag 37 fits down through the central opening of the ring with its upper edge seated on shoulder 26. Bag 37 is filled with a liquid-imbibing composition 38. A disc of semipermeable membrane 39 extends across and closes the opening of bag 37 with its edge seated on shoulder 35. Finally, a locking washer 40 fits into channel 33 and seats on shoulder 34 to compress the edges of the bag and membrane.

Manually instigated axial movement of subassembly 22 toward end 14 is achieved through cooperative engagement between ring 32, washer 23, and end cap 24. Washer 23 is sandwiched between the top flat edge of the ring and the bottom flat edge of the end cap. It is the means by which rotation of the end cap is translated into axial movement of the subassembly. Specifically, such movement is effected by inserting a key or tool (not shown) into keyway 43 in the top of the end cap and twisting the end cap so that its screws into the housing. Since the washer surface is such that there is little friction between it and the end cap, the force component on the washer that is generated by twisting the cap is primarily axial. That force is in turn transmitted to the subassembly thereby driving it in piston-like fashion toward end 14 of the housing.

Pump 11 is used and operates as follows. Starting with the pump disassembled (as in FIG. 2), the composition to be pumped such as a pharmaceutical composition 25a is charged into the housing lumen. Subassembly 22 is then inserted into the housing follwed by the insertion of washer 23. The osmotically active preferrably aqueous liquid 27 in any of the forms previously noted is then charged into compartment 26 and the end cap is screwed into the open end of the housing. The thus assembled pump is then placed on the skin with outlet 19 in the form of a needle penetrating the cutaneous layer and end 14 lying substantially flush against the skin as shown in FIGS. 1 and 3 or connected to a catheter or tube as shown in FIG. 7. As soon as the liquid 27 is charged into compartment 26 it begins to be imbibed from compartment 26 through the semipermeable membrane into bag 37. Ambient pressure is maintained on the liquid by means of a vent 44 that extends through the end cap. The vent is filled with a material that is permeable to air but not permeable to the liquid. The imbibition of liquid in bag 37 is caused by an osmotic imbalance between the liquid and the composition 38. The influx of liquid into the bag causes the bag to expand (shown in phantom and indicated by the axially directed arrow in FIG. 3) into compartment 25 and thereby displace the composition therefrom via the outlet 19 to the site of use. The rate of liquid influx per unit area of semipermeable membrane will depned upon the composition and thickness of the membrane and the magnitude of the osmotic imbalance (this assumes insignificant back pressure from the bag). By keeping the osmotic imbalance substantially constant, the influx will be constant and so will the rate of injection of the pharmaceutical composition. Such operation is called "steady state" or "tonic" operation and is characterized by a controlled constant rate of injection at a predetermined baseline level.

The tonic mode of operation may be disrupted and the baseline level of administration supplemented with a pulse administration by manually instigating axial movement of subassembly 22 toward end 14 in the manner described above. Such movement exerts pressure on composition 12 and causes it to be discharged more rapidly. The magnitude and duration of the pulse will depend upon the extend to which the end cap is screwed into the housing. The length of the threads on the inner edge of the housing and/or shoulder 17 will limit the extend of axial movement of the subassembly. The supplemental pulse mode or "phasic" operation may be instigated one or more times depending upon the dosage regimen that is desired.

The components of the pump may be made from well known materials. The housing and end cap may be made from metals or plastics that are inert relative to the liquids they contact and are preferably not irritating to the skin. Examples of such materials are stainless steel, aluminum, polyolefins such as polypropylene and polyethylene, polyesters, polyamides, and polycarbonates. The outlet 19 when a needle is preferably made of stainless steel and has a gauge in the range of 25 to 32. The support ring of the subassembly may be made from the same materials as are the housing and end cap. The semipermeable membrane of the subassembly may be made from cellulose esters and ethers, such as cellulose acetate and cellulose butyrate and other semipermeable film-forming compositions disclosed in U.S. Pat. No. 3,760,984 at col 4, line 53 to col 5, line 39 and in U.S. Pat. No. 3,995,631 at col 7, line 40 to col 8, line 15, which disclosures are incorporated herein by reference. Such materials may contain minor amounts of additives such as fillers, stabilizers, pigments, water flux enhancers, and water flux attenuators. The expandable bag of the subassembly may be made from impermeable materials such as latex rubber, polyisoprene, stryene-butadiene copolymers, butyl rubber, and nitrile rubber that are expandable by virtue of their elastomeric properties. Such elasticity may be facilitated by the formation of corrugations in the side walls of the bag. A less desirable alternative is to make the bag from an inelastic material that is rendered expandable by virtue of a bellows structure. The low friction washer that rests between the support ring and end cap may be made from materials such as polypropylene and polytetrafluoroethylene (sold under the trademark TEFLON).

The composition 25a must be in a flowable form such as a solution, dispersion, colloidal mixture, or low viscosity gel. When a pharmaceutical it will normally be composed of an active pharmaceutical agent combined with a suitable diluent, typically a solvent for the agent. It may also contain minor amounts of innocuous additives such as stabilizers, viscosity modifiers, immunosuppressants, and the like. As used herein the term "pharmaceutical" is intended to include agents that have a pharmacological, physiological, or nutritional effect at the sites to which they are delivered.

The liquid-imbibing agent that fills the expandable bag may be an osmotically effective agent (a compound that exhibits a relatively high osmotic pressure when in solution) such as the solutes disclosed in U.S. Pat. No. 4,034,756 at col 12, lines 55 to 61, which disclosure is incorporated herein by reference. Sodium chloride and potassium chloride are preferred solutes. Alternatively the liquid-imbibing agent may be a compound that is insoluble or partly soluble in water that is capable of absorbing liquid and swelling in response thereto to increase in volume, typically at least two fold. Examples of such compounds are disclosed in U.S. Pat. No. 4,180,073 at col. 4, lines 14 to 38 and U.S. Pat. No. 4,207,893 at col. 4, lines 23 to 47, which disclosures are incorporated herein by reference.

The liquid that is charged to compartment 24 may be in the form of either a liquid, preferably water, or a gel such as a hydrogel and may be absorbed on a wick or mat. Cosolvents that are also capable of diffusing through the semipermeable membrane may be admixed with the liquid if desired. Minor amounts of additives that do not elevate the osmotic pressure of the liquid significantly may also be included in the liquid.

Figure 4:
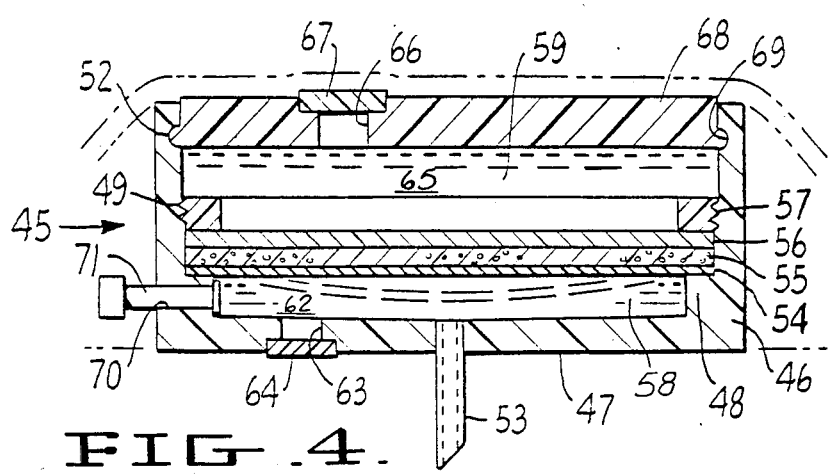
FIG. 4 is an enlarged sectional view of another embodiment of the invention.

FIG. 4 shows an embodiment of the pump, generally designated 45. Pump 45 includes a hollow housing 46 that has an integral end wall 47 that defines the basal surface of the housing has a shoulder 48 hear the end wall, a threaded segment 49 located about midway on the surface, and a way 52 located near the edge of the open end of the housing. Outlet 53 extends through the end wall and opens into the lumen of the housing. It has the same function and structure as outlet 19 of injector 11. Within the housing lumen a 3-layer subassembly composed of an elastic impermeable membrane 54, a disc of water-imbibing material 55, and a rigid semipermeable membrane 56 is supported on shoulder 48. These components of the subassembly have the same composition and function as wall 37, composition 38, and membrane 39, respectively, of injector 11. An externally threaded locking ring 57 is received in the threaded segment 49 to compressively fix the edge of the subassembly.

The subassembly divides the housing lumen into two compartments: one, designated 58, contiguous to the elastic mambrane and the other, designated 59, contiguous to the semipermeable membrane. Compartment 58 holds a composition 62 that may be charged thereto before the subassembly is placed into or thereafter by injection through opening 63 and septum 64 located in wall 47. Compartment 59 holds an aqueous liquid 65 that may be charged thereto after the subassembly is placed into the housing or thereafter by injection through an opening 66 and a septum 67 in end cap 68. The end cap has a splay 69 at the lower edge of its cylindrical surface that snap fits into way 52 to cap the open end of the housing.

Pump 45 operates in a manner similar to pump 11 with a few significant variations. Water from the aqueous liquid is imbibed through the semipermeable membrane by the water-imbibing composition 55. Since impermeable membrane 54 is in the form of a sheet rather than a bag, the influx of water into the space between it and the semipermeable membrane causes it to inflate arcuately (shown in phantom in FIG. 4) rather than expand linearly as does bag 37. The inflation or bowing of the membrane displaces pharmaceutcal composition from the pump via the outlet 53. Such displacement is at a substantially constant rate in accordance with the discussion of the operation of pump 11, supra. Unlike pump 11, however, phasic operation of injector 45 is not achieved by moving the subassembly axially. In this regard the end cap and subassembly of pump 45 are fixed and are not moveable axially except for disassembly purposes. Instead, phasic operation is effected by means of a radial opening 70 in the sidewall of the housing that opens into compartment 58 and a manually operable piston 71 that fits into opening 70. By depressing the piston inwardly, pressure is exerted on the composition causing its rate of discharge from the pump to increase. The inclusion of opening 70 and piston 71 in pump 45 is optional. Without them the pump is capable of only tonic operation.

Figure 5:
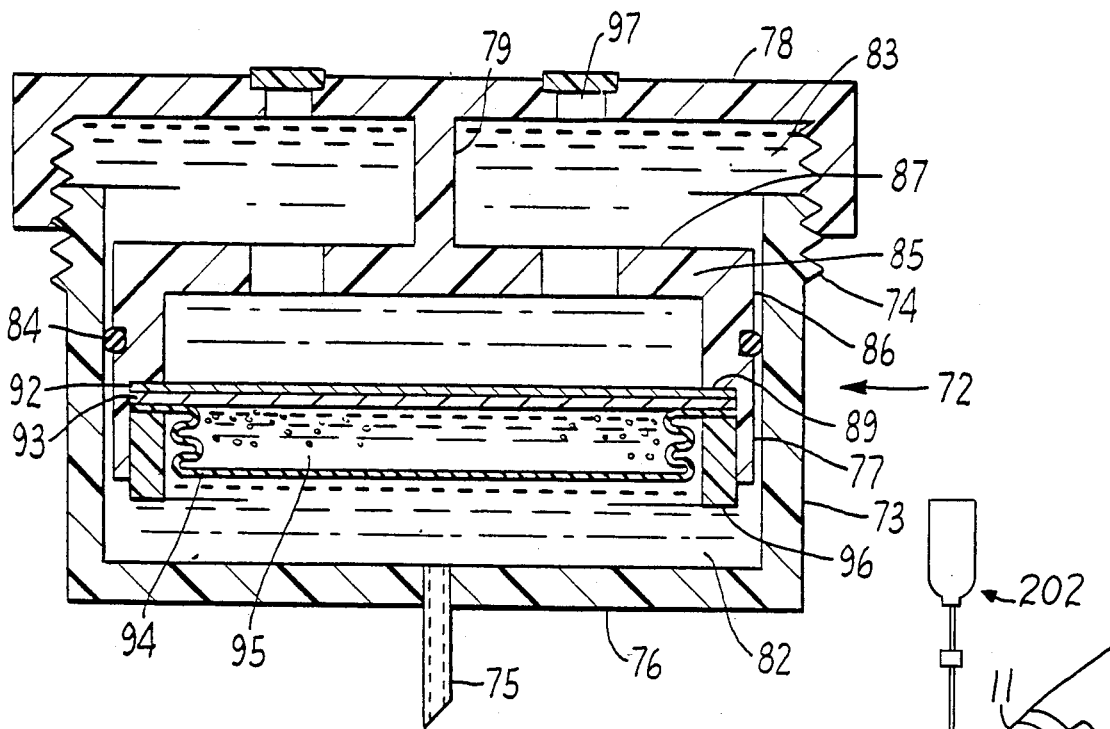
FIG. 5 is an enlarged sectional view of yet another embodiment of the invention.

FIG. 5 illustrates another embodiment, designated 72, that is capable of both tonic and phasic operation. Housing 73 of the pump has a threaded segment 74 on the open end edge of its outer cylindrical surface and outlet 75 extending through its integral end wall 76. An axially slideable water-imbibing subassembly 77 is received in the housing lumen and is integrally connected to an interior threaded end cap 78 by an axial rib 79. Subassembly 77 divides the housing lumen into a pharmaceutical composition-containing compartment 82 contiguous to the end wall and an aqueous liquid-cntaining compartment 83 contiguous to the end cap. An O-ring 84 carried in a channel on the outer side of the subassembly forms a seal between the two compartments.

Subassembly 77 is composed of a cylindrical inverted cup-shaped support member 85 having a cylindrical sidewall 86 and an integral end wall 87 that has a pair of axial holes 88 in it. The inner surface of the side wall has a shoulder 89 on which a semipermeable membrane 92, a porous membrane support 93, and a flexible impermeable bag 94 containing a water-imbibing composition 95 are carried. A locking ring 96 compresses the edge of the membrane-support-bag combination against the should and is fused or otherwise affixed to the inner surface of wall 86.

Pump 72 operates in the following manner. Starting with the pump disassembled, the pharmaceutical composition is placed into the housing, the subassembly is inserted into the housing, and the end cap is partly threaded onto the open end of the housing. Compartment 83, which is defined by the space within the support member above the semipermeable membrane, the axial holes in the end wall of the support member, and the space between the support member end wall and the end cap, is filled with the aqueous liquid via either of a pair of septum blocked vents 97 in the end cap. The pump is then placed on the skin or otherwise connected to the delivery site. Water is imbibed from compartment 83 through the semipermeable membrane and underlying support into the flexible bag, causing the bag to expand into compartment 82 and displace the pharmaceutical composition therefrom via the outlet at a constant rate. Phasic operation is effected simply by threading the end cap further onto the housing. This action forces the subassembly of the injector toward wall 76 because the end cap and subassembly are connected integrally by rib 79. The resulting increased pressure on the pharmaceutical composition causes it to flow from the pump at an increased rate.

Figure 6:
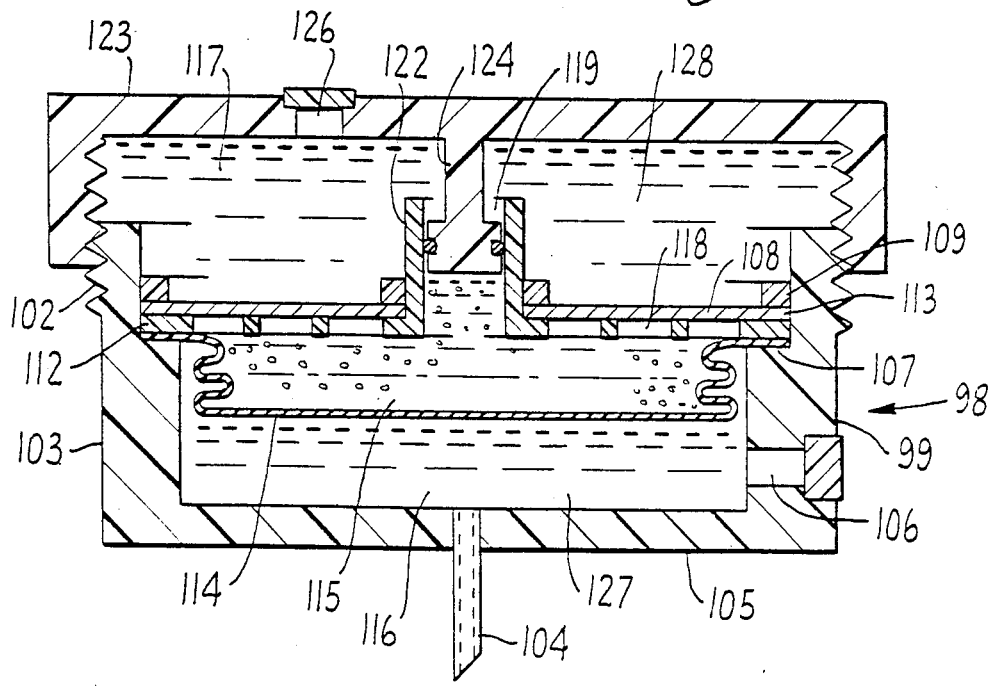
FIG. 6 is an enlarged sectional view of still another embodiment of the invention.

FIG. 6 describes another embodiment, generally designated 98, that provides tonic and phasic delivery. Its cylindrical housing 99 has threads 102 on the exterior upper edge of its cylindrical side wall 103 and outlet 104 extending through its basal end wall 105. The housing also has a septum blocked radial opening 106 through its side wall and a inner shoulder 107. A fixed water-imbibing subassembly 108 is compressively seated on the shoulder by means of a locking ring 109. Subassembly 108 consists of a support disc 112 that is sandwiched between a semipermeable membrane 113 and an expandable impermeable bag 114 that contains a water-imbibing composition 115. As in the above described embodiments, the subassembly divides the housing lumen into a composition to be pumped containing compartment 116 and an aqueous liquid-containing compartment 117. The support disc has a series of spaced axial openings 118 that are covered on one side by the semipermeable membrane and open on the other side into the expandable bag and a large axial central opening 119 that is defined by an integral axially elongated collar 122. The central opening opens on one side into the water-containing compartment and on the other side into the expandable bag. An internally threaded end cap 123 is threaded into the open end of the housing. The end cap has an integral piston member 124 extending from the center of the inner side of its top wall axially into the collar of the support disc of the subassembly. An O-ring 125 carried on the cylindrical surface of the piston member forms a fluid tight, axially slideable seal between the piston member and the collar. The end cap also has a septum blocked vent 126 that extends through its top wall to compartment 117.

Pump 106 is filled and operates as follows. A liquid composition 127 is injected into compartment 116 via opening 106, water 128 is injected into compartment 117 via vent 126, and the pump is placed on the skin or otherwise connected to the delivery site. Water from compartment 117 is imbibed by composition 115 through the semipermeable membrane and axial openings in the support disc into the expandable bag. This influx of water causes the bag to expand into the composition to be pumped containing compartment thereby displacing the composition from the pump at a constant rate.

Phasic operation of the pump is effected by screwing the end cap further onto the housing. This action drives piston member 124 down into the collar thereby exerting pressure on composition 115. This pressure is equalized by expansion of the expandable bag which, in turn, increases the rate of displacement of the pumped composition from the injector. Such operation is distinct from that of the previously described injectors in that it is effected by exerting force on the contents of the expandable bag rather than by axial movement of the entire water-imbibing subassembly.

The components of the pumps depicted in FIGS. 4–6 may be made from the same materials as are the corresponding parts of the injector shown in FIGS. 1–3.

Modifications of the above-described injectors that are apparent to those of skill in the mechanical and/or medical device arts are intended to be within the scope of the following claims.

I claim:
1. A self-driven pump for dispensing a fluid composition comprising
   (a) a hollow closed rigid body;
   (b) a liquid imbibing member mounted within the body that divides the lumen of the body into a first compartment adapted to hold the fluid to be dispensed and a second compartment adapted to hold the liquid to be imbibed, the liquid imbibing member comprising:
      (i) a rigid semipermeable wall that faces the second compartment;
      (ii) an expandable impermeable wall that faces the first compartment; and
      (iii) a liquid imbibing composition contained between the rigid semipermeable wall and the expandable impermeable wall; and
   (c) outlet means extending through the wall of the body, in fluid communication with said first compartment.
2. The pump of claim 1 wherein the liquid imbibing member is mounted within the body such that the member is not capable of movement other than the expansion of said expandable impermeable wall.
3. The pump of claim 1 wherein the liquid imbibing member is able to slide toward the first compartment and the injector includes:
   (d) manually operable means for exerting a force on the member to cause it to slide within the body toward the first compartment.

4. A self-driven pump for dispensing a fluid composition comprising:
  (a) a rigid hollow housing having a cylindrical lumen, said housing being provided with means for closing the ends of the housing;
  (b) a liquid imbibing member mounted transversely within the housing that divides the lumen of the housing into a first compartment that contains the fluid composition and a second compartment that contains the liquid to be imbibed, the liquid imbibing member comprising
    (i) a rigid semipermeable wall that faces the second compartment;
    (ii) an expandable impermeable wall that faces the first compartment; and
    (iii) a liquid imbibing composition contained between the semipermeable wall and the impermeable wall; and
  (c) outlet means extending from the first compartment through the housing through which said composition may be pumped.

5. The pump of claim 4 wherein the liquid imbibing member is mounted within the housing such that the member is not capable of movement other than the expansion of the expandable impermeable wall.

6. The pump of claim 5 wherein the liquid imbibing composition is itself a liquid and the injector includes means for manually exerting pressure on said liquid imbibing composition thereby causing the expandable impermeable wall to expand.

7. The pump of claim 6 wherein the liquid imbibing member includes a support member positioned between the liquid imbibing composition and the semipermeable wall, the support member having a plurality of axial holes opening to the semipermeable wall and the liquid imbibing composition and an axial opening defined by a cylindrical axially elongated collar that extends through the semipermeable wall into the second compartment and one end of said housing is capable of being depressed axially and carries a piston member that is received in the collar, whereby when said one end of said housing is depressed pressure is exerted on the liquid imbibing composition.

8. The pump of claim 7 wherein the exterior surface of the housing proximal the end capable of axial depression is threaded and said means for closing said end has interior threads in threaded engagement therewith whereby it may be screwed onto the housing to effect said axial depression.

9. The pump of claim 4 wherein the liquid imbibing member is slideably mounted in the housing such that the member is able to slide toward one end thereof and the injector pump includes
  (d) manually operable means for exerting a force on the liquid imbibing member to cause it to slide within the housing toward said one end thereof.

10. The pump of claim 4 wherein the liquid imbibing member includes an axially slideable ring on which the semipermeable wall, expandable impermeable wall, and water imbibing composition are mounted and one of the ends of said housing is capable of being depressed axially to bear against the axially slideable ring and drive and liquid imbibing member toward said other end of said housing.

11. The pump of claim 10 wherein the interior surface of the housing provided the end capable of axial depression is threaded and said means for closing said end is in threaded engagement therewith whereby it may be screwed into the housing to effect said axial depression.

12. The pump of claim 10 including sealing means between the interior of the housing and the exterior of the axially slideable ring.

13. The pump of claim 4 wherein the liquid-imbibing member includes an axially slideable ring on which the semipermeable wall, expandable impermeable wall and liquid imbibing composition are mounted, said ring being connected to the one end of said housing which end is capable of being depressed axially thereby causing the liquid imbibing member to slide toward the other end of said housing.

14. The pump of claim 13 including sealing means between the interior of the housing and the exterior of the axially slideable ring.

15. The pump of claims 1 or 4 including (d) manually operable means for exerting pressure on the composition to be dispensed.

16. The pump of claim 15 wherein the means is an opening through the wall of the body to the first compartment and a piston that fits into the opening.

17. The pump of claims 1, 2, 3, 4, 5, 6, 7, 8, 12, 13, 14, 6, 7, 8, or 16 wherein said liquid to be imbibed is water.

18. The pump of claim 15 wherein said means for exerting pressure on the composition to be dispensed comprise fluid transmitting means extending through said wall providing fluid communication between the interior of said first compartment and externally operated pressure generating means.

19. The pump of claim 15 wherein the outlet means is in fluid communication with the interior of a live animal.

20. The pump of claims 1 or 4 wherein said outlet means is in fluid communication with the interior of the body of a live animal.

* * * * *